United States Patent [19]

Nelson

[11] Patent Number: 4,548,597
[45] Date of Patent: Oct. 22, 1985

[54] DUAL CATHETER AND METHOD FOR SEPARATELY WITHDRAWING FLUIDS FROM THE HUMAN HEART

[75] Inventor: Duane M. Nelson, Waukesha, Wis.

[73] Assignee: Minnesota Mining and Manufacturing Company, St. Paul, Minn.

[21] Appl. No.: 590,637

[22] Filed: Mar. 19, 1984

[51] Int. Cl.$^4$ ............................................ A61M 1/03
[52] U.S. Cl. ............................................... 604/43
[58] Field of Search ...................... 604/43, 44, 45, 19, 604/27

[56] References Cited

U.S. PATENT DOCUMENTS 4,037,599  7/1977  Raulerson ................. 128/214.4
4,129,129  12/1978  Amrine ...................... 604/43

OTHER PUBLICATIONS

W. J. Kolff, M.D., "Transapical Left Ventricular Bypass", *Archives of Surgery*, vol. 103, p. 656 (Letters to Editor), Nov. 1971.

Dr. John C. Norman, M.D., F.C.C.P., "A Single Cannula for Aortic Perfusion and Left Ventricular Decompression", *Chest*, vol. 58, No. 4, pp. 378-379 (Progress in Cardiovascular Surgery), Oct. 1970.

Paul C. Taylor, M.D. and Donald B. Effler, M.D., "Management of Cannulation for Cardiopulmonary Bypass in Patients with Adult-Acquired Heart Disease", *Surgical Clinics of North America*, vol. 55, No. 5, pp. 1205-1215 (Symposium on Surgical Techniques), Oct. 1975.

William I. Brenner, M.D., et al, "Nonthrombogenic Aortic and Vena Caval Bypass Using Heparin-Coated Tubes", *The American Journal of Surgery*, vol. 127, pp. 555-559, May 1974.

Tsuguhito Tanaka, M.D., et al, "Transapical Aortic Perfusion with a Double-Barreled Cannula", *The Society of Thoracic Surgeons*, vol. 25, No. 3, pp. 209-214, Mar. 1978.

"Method of Discarding Cardioplegic Solution via the Right Atrium", by John H. Rousou, M.D., & Richard M. Engelman, M.D., Journal of Thoracic Cardiovascular Surgery, 82: 938-942, 1981.

"Scavenging of Cardioplegic Solution from Right Heart to Prevent Hyperkalemia", by Ecrument A. Kopman, M.D., and Thomas B. Ferguson, M.D., The Journal of Thoracic and Cardiovascular Surgery, 86-1; 153-155, 1983.

"Persistent Electromechanical Cardiac Arrest Following Administration of Cardioplegic and Glucose-Insulin-Potassium Solutions", by Ecrument A. Kopman, M.D., & Rebecca C. Ramirez-Inawat, M.D., Anesthesia and Analgesia, 59-1: 69-71, 1980.

"High-Volume Crystalloid Cardioplegia", by Richard M. Engelman, M.D., John H. Rousou, M.D., and Stanley Lemeshow, Ph.D., The Journal of Thoracic and Cardiovascular Surgery, 86: 87-96, 1983.

*Primary Examiner*—John D. Yasko
*Attorney, Agent, or Firm*—Donald M. Sell; James A. Smith; Robert W. Hoke, II

[57] ABSTRACT

A dual catheter assembly and a method for separately withdrawing fluids from a vena cava and a right atrium of a human heart into extracorporeal equipment. The assembly includes a first catheter that can be positioned in the vena cava and a second catheter that can be simultaneously positioned in the right atrium.

7 Claims, 5 Drawing Figures

DUAL CATHETER AND METHOD FOR SEPARATELY WITHDRAWING FLUIDS FROM THE HUMAN HEART

BACKGROUND

The present invention relates generally to the field of medical catheters and more specifically to a dual catheter assembly. A method of separately withdrawing fluids from major blood vessels entering a human heart and from a right atrium of the heart are also included within the scope of the invention.

During open heart surgery and in other applications where it is desired to assist the circulatory system, a cardiopulmonary bypass machine is generally used to temporarily assume the functions of a heart and lungs. To accomplish this, tubes, known as catheters, are generally inserted into the major blood vessels entering and exiting the heart. These catheters, in turn, are connected to the cardiopulmonary bypass machine. Blood entering the heart is picked up by a catheter and directed to the cardiopulmonary bypass machine. The machine oxygenates the blood and pumps it back, through another catheter, into the major blood vessels exiting the heart. In this manner, the heart and lungs are bypassed, and the blood is still oxygenated and pumped through a patient.

The blood being bypassed is generally referred to as systemic blood. It is the blood that normally circulates from a side of the heart, through the patient generally, and returns to a right side of the heart through a superior and an inferior vena cava. Systemic blood is to be distinguished from coronary blood which circulates from the left side of the heart, through the coronary arteries and the coronary veins of the heart muscle itself, and returns to the right side of the heart through a coronary sinus. The coronary sinus is located within the right atrium of the heart.

Coronary blood, as opposed to systemic blood, is generally interrupted rather than bypassed. This interruption of blood flow can cause extensive damage to the myocardium. Several methods of providing protection for the myocardium have been developed. A common method is cold cardioplegic arrest of the heart.

The use of cold cardioplegic solutions containing high levels of potassium is a routine part of many cardiac operations. Its primary purpose is to protect the myocardium from ischemic damage during periods of coronary artery interruption. The cardioplegic solution is infused into the root of the aorta or directly into the coronary arteries from which it is then distributed throughout the myocardial muscle by the coronary arterial network. Ultimately, the cardioplegic solution drains into the right atrium of the heart through the coronary sinus.

The used cardioplegic solution entering the right atrium can generally be dealt with in either of two ways. It can be allowed to mix with the systemic blood and directed to the cardiopulmonary bypass machine, or it can be separately removed from the patient. An example of allowing mixing is disclosed in U.S. Pat. No. 4,129,129. A catheter having a small diameter inlet opening, extending beyond a main catheter entrance area, assists in the maintenance of adequate venous drainage by collecting venous blood directly from the inferior vena cava. The main catheter entrance collects the flow from the superior vena cava and the coronary sinus.

Mixing the cardioplegic solution with the blood can have disadvantages. Depending upon the cardioplegic solution used, hemodilution and hyperkalemia are two known side effects. Excessive hemodilution decreases the oxygen carrying capacity of the blood by lowering the hemoglobin levels. It also contributes to bleeding complications by decreasing the concentrations of clotting factors in the blood. Hyperkalemia has been associated with difficulties in restoring the electromechanical activity of the heart after open heart surgery.

Removing the used cardioplegic solution from the patient minimizes these side effects. One such method is described in "Method of Discarding Cardioplegic Solution via the Right Atrium," by John H. Rousou, M.D., and Richard M. Engelman, M.D., Journal of Thoracic Cardiovascular Surgery, 82:938-942, 1981. As shown in FIG. 1, the authors drain the vena cavae through two separate catheters inserted through the right atrium. An additional suture opening is made in the right atrium to provide an entry site for a third catheter. The third catheter is used to suction the cardioplegic solution draining into the right atrium through the coronary sinus. While this approach restricts mixing of the cardioplegic solution with the systemic blood, it prolongs and complicates the surgery by requiring the insertion of the third catheter through a third wound in the heart. The catheters and methods of the present invention overcome these disadvantages to achieve separate venous and coronary sinus drainage without the complication or trauma associated with the third catheter and the third wound in the heart.

SUMMARY OF THE INVENTION

According to the invention, there is provided a dual catheter assembly for separately withdrawing fluids from a vena cava and a right atrium of a human heart into extracorporeal circulation equipment. The assembly comprises first and second catheters. Each of the catheters has an inlet opening, an outlet opening, a through passageway between the openings separated from the through passageway of the other catheter, and means adjacent the outlet opening for releasably coupling the outlet opening of the catheter to the extracorporeal circulation equipment. A part of the second catheter adjacent the inlet opening of the second catheter is attached to the first catheter with the inlet of the second catheter spaced a distance from the inlet opening of the first catheter so that the inlet openings of the first and second catheters can be simultaneously positioned in the vena cava and the right atrium, respectively.

According to the invention, there is also provided a method of separately withdrawing fluids from vena cavae and a right atrium of a human heart. The method comprises the steps of providing a single catheter and a dual catheter assembly, inserting the single catheter through the right atrium and into one of the vena cavae, inserting the dual catheter assembly through the right atrium and into another of the vena cavae, and clamping the one of the vena cavae around the single catheter and the other of the vena cavae around the dual catheter assembly so that mixing of the fluids is restricted.

BRIEF DESCRIPTION OF THE DRAWINGS

The present invention will be further described with reference to the following drawings wherein like numerals refer to like parts, the accompanying description and the appended claims.

DETAILED DESCRIPTION

Figure 1:
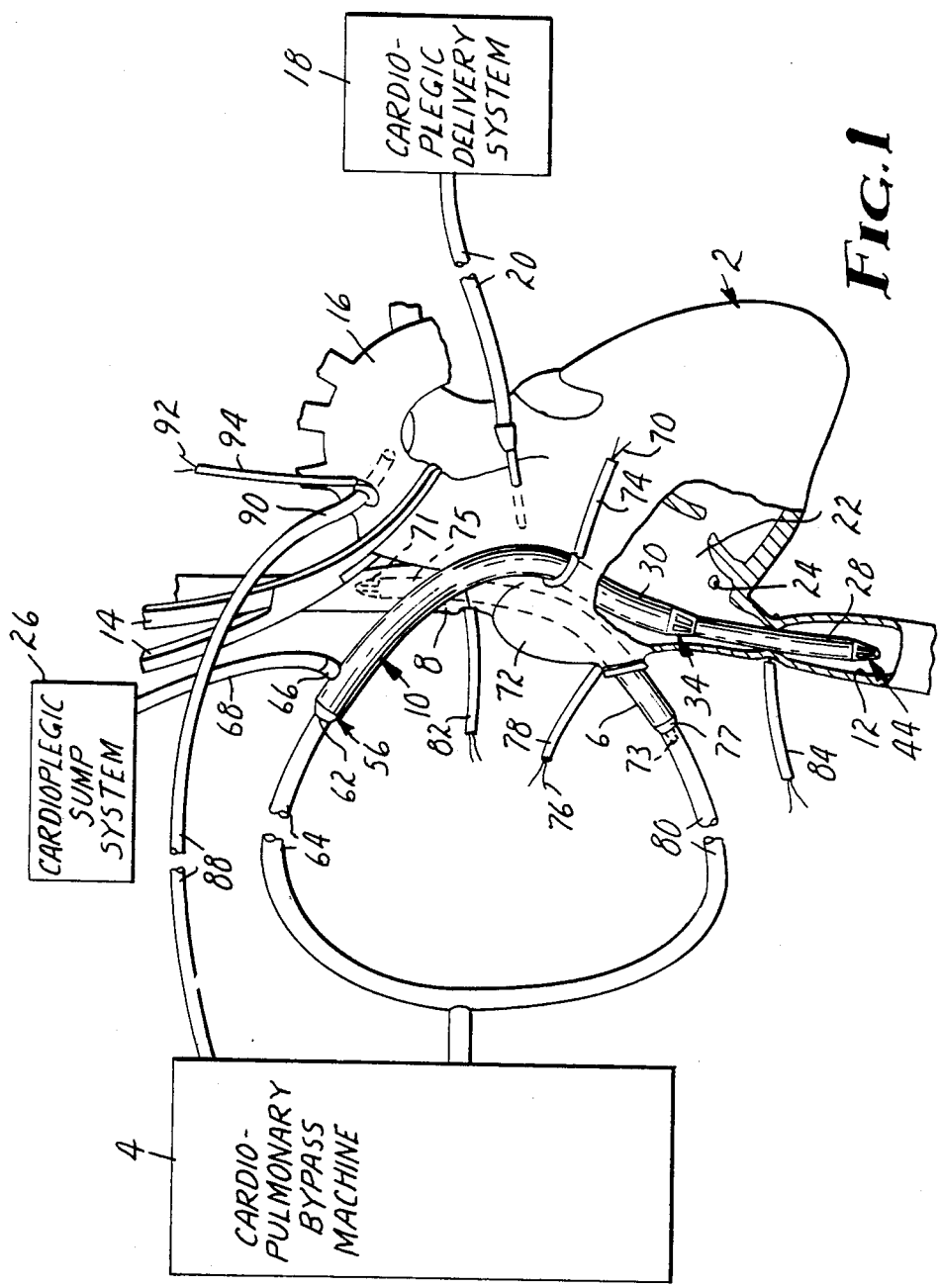
FIG. 1 is a schematic illustration of a dual catheter assembly according to the present invention being used in a method of the present invention for separately withdrawing fluids from the vena cavae and from the area of the coronary sinus within the right atrium of the heart.

Referring now to FIG. 1 of the drawings, there is schematically shown a human heart 2 that has been arrested and its functions assumed by a cardiopulmonary bypass machine 4. The bypass machine 4 is conventional and includes a suitable blood oxygenator, a temperature probe, a pressure monitor, an arterial pump, an arterial filter and an air bubble detector. The bypass machine 4 is connected to the heart 2 by a conventional, single catheter 6 disposed within a superior vena cava 8 and a dual catheter assembly 10 of the present invention disposed within an inferior vena cava 12 in a manner to be described. Although it is preferred to drain the superior vena cava 8 with the conventional catheter 6 and the inferior vena cava 12 with the dual catheter assembly 10, they can be reversed, and nothing herein is meant to limit the use of the dual catheter assembly 10 to either one of the two vena cavae.

During ischemic arrest, a standardized technique of administering crystalloid cardioplegic solution is used to protect the heart 2. A cross-clamp 14 is typically applied across the aortic arch 16. Cardioplegic solution is administered via a conventional cardioplegia delivery system 18 into the root of the aorta 16 or directly into the coronary arteries, not shown, through a suitable cardioplegia catheter 20. The cardioplegic solution is administered periodically to maintain ischemic arrest as determined by the attending surgeon. It is distributed through the heart 2 by the coronary arterial network, not shown, to arrest the heart 2 and to reduce the metabolic requirements of the heart 2. From the coronary arterial network, the cardioplegic solution circulates through the coronary venous system, not shown, and eventually drains into a right atrium 22 of the heart 2 through a coronary sinus 24. From the right atrium 22, the cardioplegic solution is periodically withdrawn through the dual catheter assembly 10 by a cardioplegia evacuation system 26 in a manner to be described.

Figure 2:
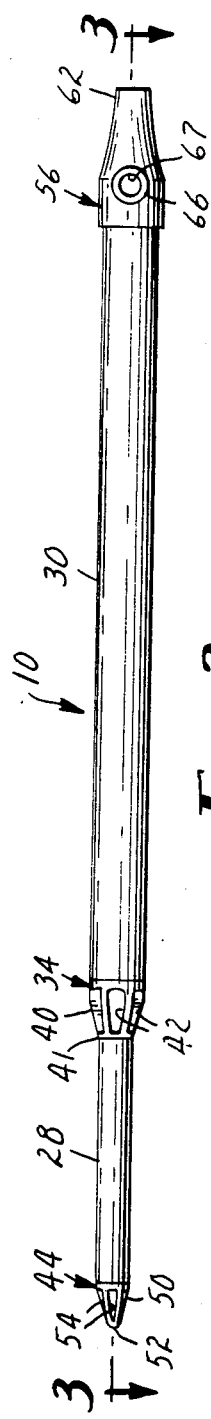
FIG. 2 is a side view of the dual catheter assembly of the present invention shown in FIG. 1.
Figure 3:
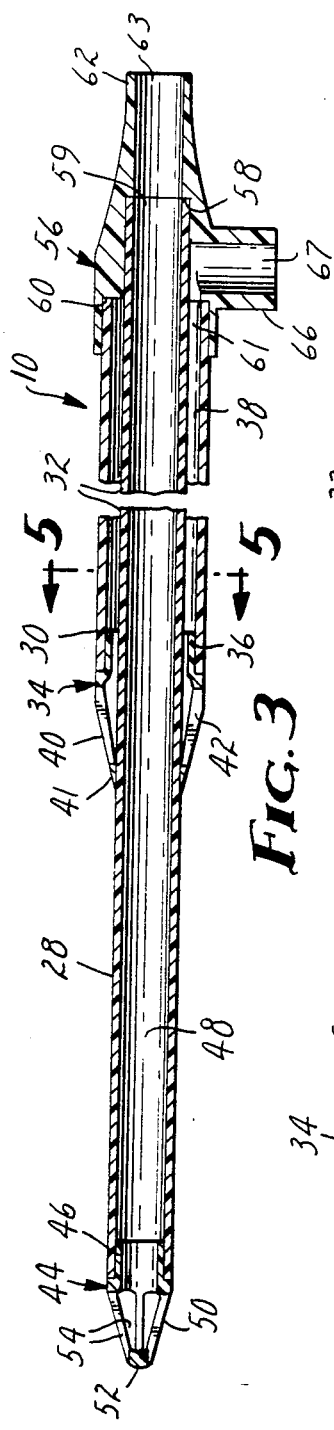
FIG. 3 is an enlarged, cross-sectional view taken approximately along line 3—3 of FIG. 2.
Figure 5:
FIG. 5 is an enlarged cross-sectional view taken approximately along line 5—5 of FIG. 3.

Referring now to FIG. 2, there is shown a side view of the dual catheter assembly 10 used to drain the inferior vena cava 12 and the right atrium 22 as shown in FIG. 1. The assembly 10 includes a first catheter 28 and a second catheter 30. Catheters 28 and 30 are preferably cyclindrical. The first catheter 28 includes a portion 32 preferably coaxially disposed within the second cathether 30 as best shown in FIG. 3 and FIG. 5. However, the portion 32 can be otherwise disposed within the second catheter 30, or not disposed within the second catheter 30 at all. For example, the portion 32 of the first catheter 28 can be longitudinally aligned with the second catheter 30 in a side-by-side relationship as long as the resulting, outside shape of the dual catheter assembly is maintained substantially cyclindrical.

Figure 4:
FIG. 4 is an end view of the dual catheter assembly of FIG. 1.

Referring to FIGS. 2, 3 and 4, the first catheter 28 is connected to the second catheter 30 at an inlet portion 34. The inlet portion 34 includes a telescopic reducer flange 36 projecting within a passageway 38 of the second catheter 30 and a tapered body 40 circumscribing the first catheter 28. The passageway 38 preferably has an inside diameter of about 1.4 centimeters and most preferably 1.43 centimeters. The tapered body 40 includes a plurality of elongated, longitudinally extending openings 42 there through that are preferably equally spaced about the circumference of the tapered body 40 and adapted to pass the flow of coronary sinus drainage from the right atrium 22 of the heart 2 into the passageway 38 of the second catheter 30.

The first and second catheters 28 and 30 are preferably comprised of a suitable biomedical grade tubing. The inlet portion 34 is preferably molded from a conventional rigid polyvinylchloride material. The first catheter 28 is preferably heat sealed, solvent cemented or otherwise joined to the inlet portion 34 adjacent the tapered body 40 at joint 41 to produce a liquid-impervious seal therebetween. The second catheter 30 is similarly joined to the inlet portion 34 at flange 36.

The first catheter 28 coaxially extends beyond the inlet portion 34 and terminates at an inlet portion 44. The distance between the inlet portions 34 and 44 is preferably in the range of about 5 to 10 centimeters and most preferably 5.1 to 10.1 centimeters. The inlet portion 44 includes a telescopic reducer flange 46 projecting within a passageway 48 of the first catheter 28 and a tapered body 50 terminating at a rounded tip 52. The passageway 48 preferably has an inside diameter of about 0.9 centimeters and most preferably 0.876 centimeters. The tapered body 50 includes a plurality of elongated, longitudinally extending openings 54 there through that are preferably equally spaced about the circumference of the tapered body 50 and adapted to pass the flow of systemic blood from the inferior vena cava 12, as shown in FIG. 1, or the superior vena cava 8 into the passageway 48 of the first catheter 28. The inlet portion 44 is preferably molded from a conventional, rigid polyvinylchloride material and heat sealed, solvent cemented or otherwise joined to the first catheter 28 at flange 46.

The opposite end of the dual catheter assembly 10 terminates in a connector 56. The connector 56 includes a first recess 58 receiving an outlet opening 59 of the first catheter 28 and a second recess 60 receiving an outlet opening 61 of the second catheter 30. A first cyclindrical coupler 62 passes the flow of systemic blood from the outlet opening 59 of the first catheter 28, through a passageway 63 in the connector 56 and into suitable connecting tubing 64 leading to the cardiopulmonary bypass machine 4 as shown in FIG. 1. A second cyclindrical coupler 66 passes the flow of coronary sinus drainage, in this case used cardioplegic solution, from the outlet opening 61 of the second catheter 30, through a passageway 67 in the connector 56 and into suitable connecting tubing 68 leading to the evacuation system 26 as also shown in FIG. 1. The couplers 62 and 66 preferably releasably couple with the tubing 64 and 68, respectively, in conventional fashion. The connector 56 is preferably molded from a conventional, rigid polyvinylchloride material and heat sealed, solvent cemented or otherwise joined to the first catheter 28 at the first recess 58 and to the second catheter 30 at the second recess 60. Although the connector 56, the inlet portion 34 and the inlet portion 44 have been shown and described as separate parts, they can be molded or otherwise formed or made with the catheters 28 and 30 as one piece.

Referring now to FIG. 1, the manner in which the dual catheter assembly 10 is used with the conventional catheter 6 to withdraw fluids from the inferior vena cava 12, the coronary sinus 24 and the superior vena cava 8 through the right atrium 22 of the heart 2 will next be described. For the purposes hereof, the catheter 6 can be any suitable and conventional single catheter consistent with good surgical technique. It has an inlet opening 71, an outlet opening 73, a through passageway 75 between the openings 71 and 73, and a cylindrical coupler 77 adapted to releasably couple the catheter 6 to a tubing 80. The use of any particular size of catheters is a matter of individual medical judgment based on training and experience.

Referring to FIG. 1, the dual catheter assembly 10 is introduced into the inferior vena cava 12 through the right atrium 22. This is preferably accomplished by placing a conventional purse string suture 70 around the right atrial appendage 72 and drawing the suture 70 through a rubber ligature tube 74 as more fully shown and described in U.S. Pat. No. 4,129,129 at Col. 2, Lines 51-68 and Col. 3, Lines 1-4, which is hereby incorporated by reference. A vascular clamp, not shown, is used to isolate the purse string while the end of the appendage 72 is amputated.

The atriotomy opening is exposed with clamps, not shown, and the dual catheter assembly 10 partially inserted. The occluding vascular clamp is released and the assembly 10 quickly inserted into the right atrium 22 and directed toward the inferior vena cava 12 to prevent blood loss. The inlet portion 44 of the first catheter 28 is advanced into the inferior vena cava 12 until the inlet portion 34 of the second catheter 30 is centrally located in the right atrium 22 as shown in FIG. 1.

The clamps are removed, and the purse string suture 70 tightened as shown in FIG. 1. Preferably, the ligature tube 74 is tied to the dual catheter assembly 10 to keep it out of the way during the surgical procedure. The first coupler 62 of the connector 56 is attached to the tubing 64 and the second coupler 66 of the connector 56 is attached to the tubing 68.

The conventional, single catheter 6 is similarly introduced into the superior vena cava 8. A purse string suture 76 is placed in the right atrium 22. It is drawn through a rubber ligature tube 78. The suture 76 is isolated with a vascular clamp, not shown, and the right atrium 22 is incised within the suture 76. The atriotomy opening is exposed with clamps, not shown, and the catheter 6 is partially inserted. The occluding vascular clamp is released, and the catheter 6 is quickly inserted into the superior vena cava 8. The purse string suture 76 is tightened, and the ligature tube 78 is tied to the first catheter 6. The first catheter 6 is connected to tubing 80 in conventional fashion.

Tourniquets or umbilical tapes 82 and 84 are tightened around the superior vena cava 8 and the inferior vena cava 12, respectively, to clamp the superior vena cava 8 adjacent the inlet opening 71 of the conventional catheter 6 and to clamp the inferior vena cava 12 adjacent the inlet portion 44 of the dual catheter assembly 10. This effectively isolates the right atrium 22 from the venous return blood and prevents the mixing of systemic blood and coronary sinus drainage.

After initation of cardiopulmonary bypass, systemic blood draining into the conventional catheter 6 through the inlet opening 71 and into the dual catheter assembly 10 through the inlet portion 44 is directed to the cardiopulmonary bypass machine 4 by tubing 80 and 64, respectively. At bypass machine 4, the blood is oxygenated, treated and pumped in conventional fashion through tubing 88 and through a standard arterial catheter 90 into the aortic arch 16. The arterial catheter 90 is conventionally secured by a purse string suture 92 and a ligature tube 94. At the same time, cardioplegic solution is provided by the delivery system 18 through the catheter 20 in conventional fashion, circulates through the heart 2, drains into the dual catheter assembly 10 through the inlet portion 34 of the second catheter 30, and is directed to the evacuation system 26 by tubing 68. After the surgical procedure is completed, the catheters 6 and 90 and the dual catheter assembly 10 are removed, and the purse string sutures 76, 70 and 92 are tied.

The above-described method of withdrawing fluids from the vena cavae 8 and 12 and the right atrium 22 of the heart 2 can be used in other procedures in which evaluation of coronary sinus drainage is desired. The data collected can be valuable information in determining the metabolic state of the myocardium. In such instance, the coupler 66 of the connector 56 serves as a sample collection port and connects to a suitable sample reservoir to allow for collection and analysis.

What is claimed is:

1. A dual catheter assembly for separately withdrawing fluids from a vena cava and a right atrium of a human heart into extracorporeal circulation equipment, said assembly comprising:
   a. first and second catheters, each of said catheters having an inlet opening, an outlet opening, a through passageway between said openings separated from the through passageway of the other catheter, and means adjacent said outlet opening for releasably coupling said outlet opening of said catheter to said extracorporeal equipment; and
   b. a part of said second catheter adjacent said inlet opening of said second catheter attached to said first catheter with said inlet of said second catheter spaced a distance from said inlet opening of said first catheter so that said inlet openings of said first and second catheters can be simultaneously positioned in said vena cava and said right atrium, respectively.

2. The dual catheter assembly according to claim 1 wherein said first and second catheters are cyclindrical adjacent said inlet openings.

3. The dual catheter assembly according to claim 2 wherein said first and second catheters are coaxial adjacent said inlet openings, with said first catheter disposed within said second catheter.

4. The dual catheter assembly according to claim 3 wherein said first catheter has an inside diameter of about 0.9 centimeters between said inlet openings, said second catheter has an inside diameter of about 1.4 centimeters adjacent said inlet opening of said second catheter, and the distance between said openings is in the range of about 5 to 10 centimeters.

5. A method of separately withdrawing fluids from vena cavae and a right atrium of a human heart, said method comprising the steps of:
   a. providing a single catheter having an inlet opening, and outlet opening, a through passageway between said openings, and means adjacent said outlet opening for releasably coupling said outlet opening of said catheter to said extracorporeal circulation equipment;

b. providing a dual catheter assembly comprising: (1) first and second catheters, each of said catheters having an inlet opening, an outlet opening, a through passageway between said openings separated from the through passageway of the other catheter, and means adjacent said outlet opening for releasably coupling said outlet opening of said catheter to said extracorporeal circulation equipment; and (2) a part of said second catheter adjacent said inlet opening of said second catheter attached to said first catheter with said inlet of said second catheter spaced a distance from said inlet opening of said first catheter so that said inlet openings of said first and second catheters can be simultaneously positioned in a vena cava and said right atrium of said heart;

c. inserting said single catheter through said right atrium and into one of said vena cavae with said inlet opening of said single catheter in said one vena cava;

d. inserting said dual catheter assembly through said right atrium and into another of said vena cavae with said inlet opening of said first catheter in said other of said vena cavae and said inlet opening of said second catheter in said right atrium; and e. clamping said one of said vena cavae around said single catheter and said other of said vena cavae around said dual catheter assembly so that mixing of said fluids is restricted.

6. The method according to claim 5 wherein said fluid from said vena cavae is comprised of blood and said fluid from said right atrium is comprised of used cardioplegic solution.

7. The method according to claim 6 wherein said one vena cava is a superior vena cava and said other vena cava is an inferior vena cava.

* * * * *